United States Patent [19]

Andre

[11] Patent Number: 4,885,063

[45] Date of Patent: Dec. 5, 1989

[54] METHOD AND APPARATUS FOR OLEFIN RECOVERY

[75] Inventor: Robert S. Andre, Coopersburg, Pa.

[73] Assignee: Air Products and Chemicals, Inc., Allentown, Pa.

[21] Appl. No.: 260,345

[22] Filed: Oct. 19, 1988

Related U.S. Application Data

[63] Continuation-in-part of Ser. No. 150,816, Feb. 1, 1988, abandoned.

[51] Int. Cl.[4] .......................... C07C 7/04; F25J 3/02
[52] U.S. Cl. .......................................... 203/73; 203/87;
203/88; 62/24; 62/42; 62/43; 62/44; 202/153;
208/354; 208/361; 208/364; 585/809; 585/810
[58] Field of Search .................... 203/88, 73, 87, 78;
62/24, 23, 32, 9, 19, 16, 11, 44, 42, 36; 585/809,
800, 810; 208/352, 354, 361, 364; 202/154, 153,
176; 196/100, 106, 139, 98

[56] References Cited

U.S. PATENT DOCUMENTS

| | | |
|---|---|---|
| 1,393,248 | 10/1921 | Saunders ............................ 62/24 |
| 2,014,724 | 9/1935 | Eastman ........................... 585/809 |
| 2,514,294 | 7/1950 | Rupp ..................................... 62/27 |
| 2,617,272 | 11/1952 | Aicher ................................. 62/122 |
| 3,054,745 | 9/1962 | Forbes et al. .................... 208/364 |
| 3,429,805 | 2/1969 | Karbosky ......................... 208/361 |
| 3,542,673 | 11/1970 | Ringler ............................. 208/340 |
| 4,272,270 | 6/1981 | Higgins ............................... 62/24 |

*Primary Examiner*—Wilbur Bascomb
*Attorney, Agent, or Firm*—John M. Fernbacher; James C. Simmons; William F. Marsh

[57] ABSTRACT

A process and apparatus are disclosed for recovering olefins, particularly $C_3$, $C_4$, and $C_5$ olefins, from gaseous mixture thereof with lower-boiling components. The olefin-containing gas mixtures is compressed and cooled to yield vapor and condensate streams, the vapor stream is further cooled forming additional condensate, both condensate streams are combined and adiabatically flash evaporated, and the remaining liquid is distilled to recover the desired olefins in a liquid bottoms products. Flash vapor, and optionally the distillation vapor product, are recycled to the compression step.

17 Claims, 1 Drawing Sheet

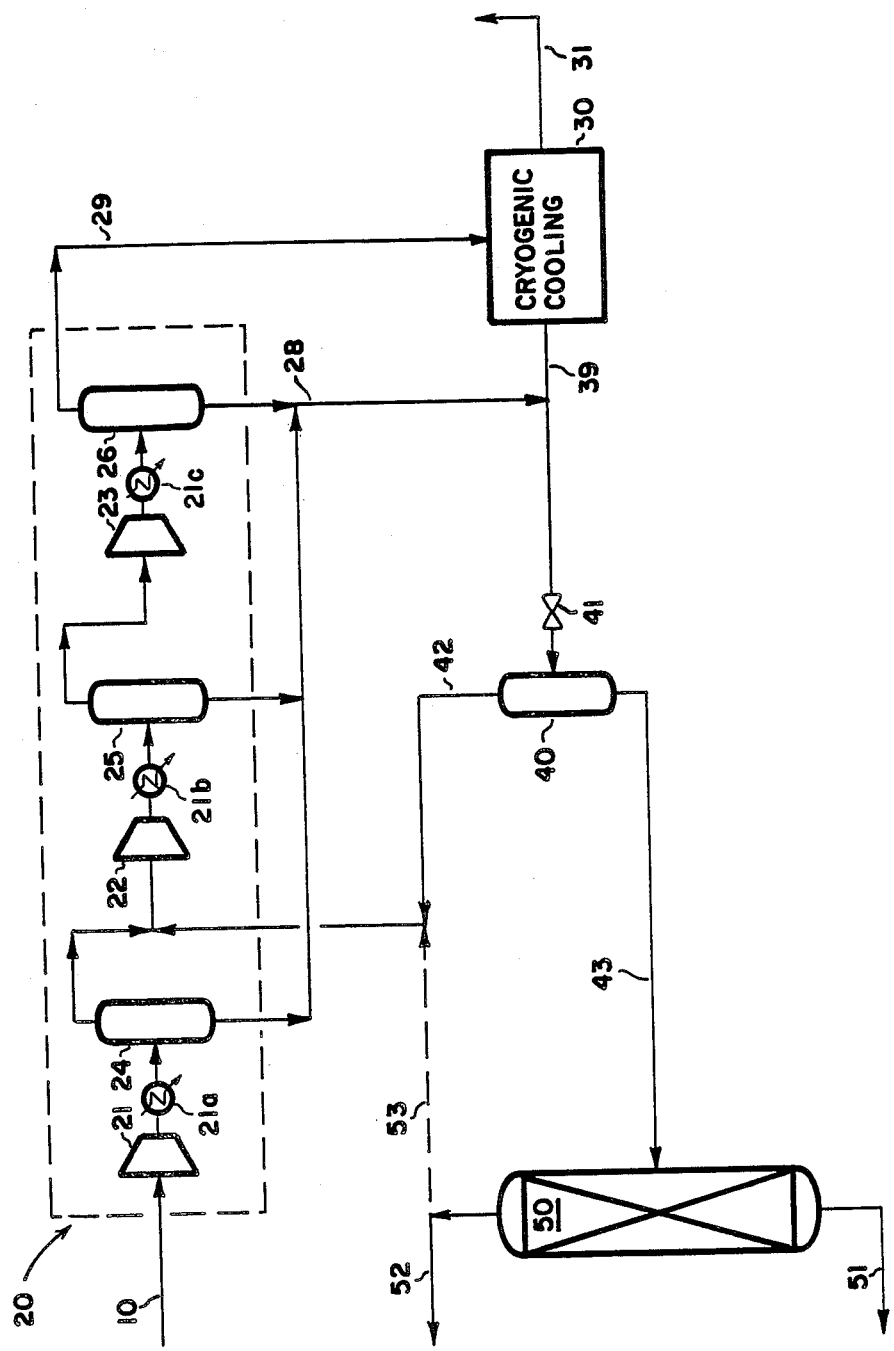

METHOD AND APPARATUS FOR OLEFIN RECOVERY

This application is a continuation-in-part of application Ser. No. 150,816, filed 1 Feb. 1988 and now abandoned.

TECHNICAL FIELD

The present invention is directed to the field of recovering olefins, in particular $C_3$, $C_4$, and $C_5$ olefins, from gas mixtures comprising such olefins and lower-boiling components. The invention has particular application in the recovery of olefins from products of the dehydrogenation of $C_3$, $C_4$, and $C_5$ paraffins.

BACKGROUND OF THE INVENTION

Olefinic products such as propylene, butylene, isobutylene, butadiene, pentene, pentadiene, and isopentadiene (isoprene) can be commercially produced by the vapor-phase catalytic dehydrogenation of propane, butanes, pentanes, or mixtures thereof. Two commercial processes for the production of olefins, for example, are the CATOFIN® and CATADIENE® processes marketed by Air Products and Chemicals, Inc., the assignee of the present invention. Typical dehydrogenation reactor vapor product contains olefinic products, unreacted and other paraffinic feed components, and various lower-boiling components including hydrogen. In the present invention, desired olefinic products are recovered from such dehydrogenation reactor products at a maximum of recovery and a minimum of capital and operating cost.

A conventional method for recovering olefinic products from dehydrogenation reactor product includes an absorption step wherein desired olefinic products as well as lower-boiling components are absorbed in a heavier hydrocarbon oil and subsequently are recovered and separated by stripping and distillation. While conventional gas plants including such an absorber-stripper separation step give a relatively clean split between the desired olefinic products and lower-boiling components, this separation method is energy intensive and thus has been largely supplanted by more economical low-temperature gas plants wherein product recovery is effected by means of compression, cooling, condensation, phase separation, and direct distillation, without the use of absorber-stripper units. In such low-temperature gas plants the feed gas is compressed, and the compressed vapor stream containing desired olefinic products and lower-boiling components is cooled by refrigeration to condense most of the desired products plus some lower boiling components. This condensate is then combined with olefin-rich condensate from the compression step and is separated by distillation to yield a liquid olefinic product and a vapor overhead containing mostly lower-boiling components and a small but significant amount of the desired olefinic products. To increase recovery of these valuable olefinic products, for example in the production of butadiene, this vapor overhead is recycled to the compression step, recompressed, and again cooled as earlier described. This recycling causes lower-boiling components to build up in the process, increasing the required size of the distillation tower and the cost of compression. In other cases, such as in the recovery of isobutylene, the distillation tower vapor overhead is taken directly as a secondary product and some valuable isobutylene product is lost.

Other low-temperature gas separation processes disclosed in the prior art have utilized various process configurations to separate and recover light hydrocarbons and lower-boiling components. In some cases, these light hydrocarbons have included olefins.

In U.S. Pat. No. 2,014,724, a process is disclosed for recovering olefins from petroleum refining gases and product gases from the thermal cracking of $C_2$ to $C_4$ paraffins. The process sequence includes compression, cooling, and phase separation to yield a gas stream of $C_4$ and lighter components. This stream is cooled by heat exchange with other process streams and is separated by distillation, or absorption and distillation, into close-boiling fractions of paraffins and olefins having the same carbon number. Olefins are recovered from these fractions chemically and the remaining paraffins are thermally cracked and recycled to the beginning of the process.

A process for recovering olefins produced by thermal cracking of gas oil is described in U.S. Pat. No. 2,514,294 wherein the gas product from cracking is compressed, cooled, and separated into a first vapor and a first liquid stream. This first liquid stream is contacted with a heavier liquid stream from the gas oil cracker in an absorber-fractionator, from which are taken a $C_3$ and lighter vapor stream and a $C_4$–$C_5$ hydrocarbon stream containing most of the diolefins produced by the cracking process. The $C_3$ and lighter stream is combined with the first vapor stream, caustic washed and dehydrated, and fractionated to recover ethylene and propylene products. $C_4$ olefins and diolefins are recovered separately by distillation. The key improvement disclosed in this reference is the recovery of $C_4$–$C_5$ hydrocarbons, especially diolefins, prior to the caustic treatment, dehydration, and fractionation of $C_3$'s and lighter components.

U.S. Pat. No. 2,617,272 discloses a low-temperature separation process for the recovery of methane, ethane, ethylene, and propylene from a gas stream comprising these components with lesser amounts of hydrogen, propane, and higher boiling hydrocarbons. The process comprises compression, cooling, and partial liquefaction, followed by separation of the resulting liquid in three distillation columns in series operating at successively higher temperatures and lower pressures to recover methane, ethane plus ethylene, and propane plus propylene. The essential feature of the disclosed process is an integrated and separated propylene recirculation system for internal heat transfer and reboiling duties. Refrigeration is provided by conventional methane, ethylene, and ammonia refrigeration circuits.

A process to recover $C_3$ to $C_5$ hydrocarbons from natural gas is described in U.S. Pat. No. 3,542,673. In this process, natural gas is compressed to ±500 psi of the mixture critical pressure; this critical pressure is typically between 1600 and 3000 psia. Refrigeration is then provided to condense all or nearly all of the hydrocarbons present in the feed. This refrigerated stream, including any uncondensed components, is subjected to a series of 4 to 10 successive adiabatic flash stages wherein intermediate liquid streams are flashed at decreasing temperatures (due to autorefrigeration) and decreasing pressures. Methane and ethane are withdrawn as vapor from each flash stage. Liquid from the last flash stage is distilled to recover the product containing propane and heavier hydrocarbons. Since olefins are almost never present in natural gas, this product stream will contain essentially non-olefinic hydrocarbons.

U.S. Pat. No. 4,272,270 discloses a cryogenic process for recovery of light hydrocarbons from refinery off-gas streams comprising mostly hydrogen and containing typically 15 mol % or less of hydrocarbons. Olefins are not present in the typical refining off-gas streams treated by the disclosed process. In the process, refinery off-gas is compressed, cooled against cold product gas and other process fluids, further cooled by external refrigeration, and separated into a first vapor and a first liquid stream. The first liquid stream is sent to a stabilizer-fractionationator column; the first vapor stream is further cooled and expanded in a series of vapor-phase expander-separators, and the resulting cooled vapor and liquid streams are also sent to the stabilizer-fractionator column. This column produces a cold hydrogen vapor product which is warmed against feed and intermediate process streams, and a liquid product comprising the recovered hydrocarbons. Temperatures in this cryogenic process range from near ambient to $-188°$ F.

These prior art processes are designed to separate products from various refinery streams or natural gas. In some of these cases, olefins are present in the feed stream or are produced in the disclosed process. The types of feed streams in these cases dictate the optimum process configurations for recovery of the products of interest. The feed streams for these disclosed processes are distinctly different from those of the present invention. While the individual components are in many cases the same, the relative amounts of these components in the typical feed stream for the process of the present invention raise unique process design problems which are addressed by the present invention.

SUMMARY OF THE INVENTION

The present invention is a process and apparatus for the efficient recovery of olefinic products, especially $C_3$, $C_4$, and $C_5$ olefins, from a vapor mixture of such olefins with lower-boiling components which may include hydrogen. This process is particularly advantageous for recovering olefins from the product gas of a catalytic dehydrogenation process.

The process of the present invention comprises compressing the feed vapor mixture in one or more compression stages, each of which consists of a compressor, an aftercooler, and a vapor-liquid separator, to provide a compressed vapor stream and a condensate stream at 100 to 500 psig and 50° to 150° F. This compressed vapor stream is further cooled by one or more refrigeration methods to yield additional condensate and a vapor stream comprising mostly lower-boiling components; the condensate is then combined with condensate from the compression step and flash evaporated at 0 to 200 psig and preferably at 50 to 150 psig. In the flash step, a vapor stream containing a large fraction of lower-boiling components and smaller fractions of olefinic products is produced and is recycled to the compression step at an appropriate stage such that the stream pressure is most nearly matched with compression stage suction pressure. The liquid fraction from the flash step is then distilled at a pressure between 50 and 450 psig to yield a liquid stream containing the desired olefinic product(s) and a vapor product containing mostly lower-boiling components and small amounts of desirable olefinic components. Optionally, for example when diolefins such as butadiene comprise the key recovered product, this distillation vapor product is recycled to the compression step along with the vapor from the flash step.

One advantage of the present invention is that the flash step allows a significant reduction of the pressure in the distillation step and the amount of lower-boiling components in the distillation feed. For example, when isobutylene is the key olefin product, the distillation tower operating pressure can be reduced from about 300 psig without the flash step to as low as 100 psig when the flash step is used.

Another advantage of the present invention is that the amount of vapor overhead to be recycled from the distillation tower to the compression step in the case of butadiene recovery is greatly reduced, which in turn significantly reduces compression costs.

A further advantage of this invention is that olefin product losses which occur when the distillation tower overhead is taken as a separate vapor product are reduced. For example, when a plant is being operated for the recovery of isobutylene, losses of this olefin product in the distillation vapor overhead are reduced by minimizing the amount of $C_4$ components needed to meet the required dew point of this vapor overhead product.

BRIEF DESCRIPTION OF THE DRAWING

The single drawing is a schematic flow diagram of the process and apparatus of the present invention for recovery of olefinic products in admixture with lower-boiling components.

DETAILED DESCRIPTION OF THE INVENTION

According to the present invention, olefinic products, in particular those olefins having three, four, or five carbon atoms, are recovered with high efficiency from mixtures comprising the desired olefinic products and lower-boiling components. The desired olefinic products include propylene, butylenes, isobutylene, butadiene, pentene, pentadiene, and isopentadiene (isoprene). Lower-boiling components which may be mixed with these olefinic products include methane, ethane, ethylene, hydrogen, carbon oxides, and nitrogen. Other hydrocarbons, especially paraffins, may be present and may include $C_3$, $C_4$, and $C_5$ hydrocarbons and small amounts of heavier components. Such gas mixtures typically are produced by catalytic dehydrogenation of paraffins to the corresponding olefins. The CATOFIN ® and CATADIENE ® processes of Air Products and Chemicals, Inc., for example, are such dehydrogenation processes.

In the present invention, as shown schematically in the drawing, feed stream 10 is compressed in compression train 20 comprising one or more compressor stages, each of which consists of a compressor, an aftercooler, and a vapor-liquid separator. The first compressor stage consists of compressor 21, aftercooler 21a, and vapor-liquid separator 24; the second stage consists of compressor 22, aftercooler 21b, and vapor-liquid separator 25; and the third stage consists of compressor 23, aftercooler 21c, and vapor-liquid separator 26. While the drawing shows three compressor stages 21, 22, and 23, a greater or lesser number of stages may be used depending on specific process requirements.

Two streams, compressed vapor stream 29 and compressor condensate stream 28, are produced by compression train 20 at 100-500 psia and 50°-150° F. Vapor stream 29 is cooled in cooling zone 30 to produce a vapor stream 31 and a liquid condensate stream 39. Sufficient cooling is provided in cooling zone 30 such that condensate stream 39 contains from 1 to 30 wt % of lower-boiling components. The remaining lower-boiling components will leave cooling zone 30 in vapor stream 31, which typically comprises methane, ethane, ethylene, and inert components, and may be used as plant fuel. The refrigeration for cooling stage 30 may be provided by one or more cooling means including work expansion of all or a portion of compressed vapor stream 29 or external refrigeration. Condensate stream 39 is then combined with condensate stream 28, this combined stream is flash evaporated adiabatically across valve 41, and the resulting fluid phases are separated in flash separator 40 to yield flash vapor stream 42 and flash liquid stream 43.

Vapor stream 42 is recycled to compression train 20 at a stage whose suction pressure most nearly corresponds to the pressure of vapor stream 42. The exact stage to which this vapor is recycled thus will vary depending on actual process conditions; for illustration, stream 42 is shown in the drawing as recycled to the second compressor 22.

Liquid stream 43 flows to distillation zone 50, which typically comprises a distillation column with multiple trays or other type of vapor-liquid contacting devices. The distillation column operates at or above the pressure of flash evaporation separator 40, typically 50 to 450 psig; this pressure is determined by the specific olefinic product to be recovered. The column is operated for example at about 50–150 psig when isoprene is to be recovered, about 100–300 psig when recovering isobutylene, up to about 100 psig (to give a maximum reboiler temperature of 150° F.) when recovering butadiene and n-butylene, and about 300–400 psig when recovering propylene. Olefinic products are recovered in liquid product stream 51. Vapor product is taken as stream 52 for cases in which this stream is relatively low in the desired olefinic product and therefore can be used as plant fuel. Such is the case in the recovery of isobutylene, for example, in which the distillation zone 50 may be operated at 100 to 300 psig; in such a case the amount of isobutylene in the vapor overhead is very low. On the other hand, when the distillation zone 50 is operated at lower pressures, for example up to about 100 psig for the recovery of butadiene and n-butylene, the distillation column overhead vapor contains sufficient butadiene to justify recycling it as stream 53 back to compression zone 20. The exact compression stage to which stream 53 is recycled will depend on actual process pressure and conditions; in the drawing, one embodiment is shown wherein the recycle stream 53 is joined with flash vapor stream 42 and sent to compressor 22.

The step of flash evaporation across valve 41 into separator 40 in the present invention greatly improves the overall efficiency of olefin recovery when compared with the previously practiced alternative process configuration. In this previous alternative, the compressor condensate stream 28 and liquid condensate stream 39 from cooling zone 30 are combined and sent directly to distillation zone 50.

In one application of the present invention, namely for the recovery of butadiene from catalytic dehydrogenation reactor effluent, use of the flash evaporation step of the present invention produces a significant amount of vapor as stream 42, comprising mostly components lighter (having lower boiling points) than butadiene. Because the amount of vapor in stream 42 does not pass through the distillation column of distillation zone 50, the operation of the column is greatly improved and the column size can be reduced over the alternative configuration. The net effect of the flash vaporization step significantly reduces the quantity of the distillation column overhead vapor stream 53 and thus reduces the cost of compression for recycle.

In another application of the present invention, for example in the recovery of $C_4$ mono-olefins such as isobutylene, product losses in the distillation vapor overhead stream 52 are significantly reduced. This reduction occurs because $C_4$ product losses are directly proportional to the amount of $C_3$ and lighter components present in the distillation zone feed stream 43, and the amount of such components in this stream is significantly reduced by the flash evaporation step of the present invention.

While the present invention as described herein is particularly useful for recovering olefins from catalytic dehydrogenation reactor effluent, it may have applications to other similar types of hydrocarbon streams containing significant amounts of components having lower boiling points than the desired product component(s). In addition, while pressures and temperatures recited are specific to the separations discussed herein, these parameters may be varied to adapt the disclosed process to the recovery of other olefinic products depending on the actual feed streams and desired products.

The advantages and process parameters of the present invention can be understood more fully by the following examples, which are based on computer-derived process simulations of two applications of the invention.

EXAMPLE 1

An isobutane-rich feed which is catalytically dehydrogenated by the commercially available CATOFIN ® process yields a product vapor stream rich in isobutylene as shown by the composition of stream 10 in Table 1 and Table 3. From this feed stream, isobutylene is to be recovered in high yield by the process of the present invention. In this example, feed stream 10 is compressed and cooled in compression train 20 (which comprises four compressor stages) to 459 psig (31.3 kg/cm$^2$ abs) and 104° F. (40° C.) to yield vapor stream 29 comprising a large fraction of the feed components lighter than isobutylene, and condensate stream 28 comprising mostly isobutylene and isobutane and containing a smaller but still significant amount of propane and lighter components. The vapor stream 29 is cooled further by adiabatic expansion in cooling zone 30 to 434 psig (29.5 kg/cm$^2$ abs) and 59° F. (15° C.) to yield vapor stream 31 rich in hydrogen and nitrogen, with smaller amounts of light hydrocarbons and inerts, and liquid stream 39 rich in isobutylene and butane but still containing small but important amounts of propane, propylene and lighter components as further shown in Table 1. After adiabatic flash evaporation of the combined streams 28 and 39 across valve 41 to 164 psig (10.5 kg/cm$^2$ abs) and 91° F. (33° C.), and separation in separator 40, vapor stream 42 is recycled to stage 22 of compression train 20 and liquid stream 45 is sent to distillation zone 50. The liquid product stream 51 between about 140° and 240° F. then contains mostly isobutane and the desired product isobutylene, which is recovered at 99.8% recovery. Vapor stream 52 from the distillation zone 50 is used as plant fuel.

EXAMPLE 2

A butane-rich feed which is catalytically dehydrogenated by the commercially available CATADIENE® process yields a vapor product shown as stream 10 in Table 2 and Table 3. This feed stream, containing the key product butadiene, is compressed and processed by the same steps as described in Example 1, except that the distillation vapor overhead stream 53 is recycled to compression train 20 and there is no vapor product 52. Key temperatures and pressures in this example are similar to those of Example 1 for streams from the compression train 20 and cooling stage 30. The flash evaporation step, however, is carried out at 74 psig (4.2 kg/cm² abs) which results in a temperature of 70° F. (21° C.) in separator 40. The distillation step is carried out at a pressure such that the reboiler temperature does not exceed 150° F. to prevent butadiene polymerization. Butadiene product is recovered in stream 51 with other C₄ hydrocarbons and sent to further separation. The amount of butadiene product recovered in stream 51 is 99.7% of that in feed stream 20.

TABLE 3

FEED COMPOSITIONS
EXAMPLES 1 AND 2 (STREAM 10)
(mol %)

| COMPONENT | EXAMPLE 1 | EXAMPLE 2 |
|---|---|---|
| $H_2$ | 34.0 | 28.6 |
| Methane | 1.9 | 2.3 |
| Ethylene | 0.2 | 1.3 |
| Ethane | 0.2 | 1.3 |
| Propylene | 2.3 | 1.7 |
| Propane | 2.0 | 0.2 |
| Isobutane | 20.9 | 0.8 |
| Isobutylene | 29.3 | 0.4 |
| Butene-1 | 0.8 | 6.8 |
| Butene-2 | — | 13.9 |
| Butadiene | 0.5 | 8.1 |
| n-Butane | 1.3 | 26.7 |
| $C_{5+}$ | 0.2 | 1.0 |
| $CO_2$ | 0.6 | 1.0 |
| CO | 0.3 | 0.3 |
| $N_2$ | 5.7 | 5.7 |

I claim:

1. A method for recovering one or more olefinic hydrocarbons, each having three, four, or five carbon atoms, from a feed stream comprising said olefinic hy-

TABLE 1

RECOVERY OF ISOBUTYLENE

| STREAMS | 10 | 28 | 29 | 31 | 39 | 42 | 43 | 51 | 52 |
|---|---|---|---|---|---|---|---|---|---|
| Composition (as flow rate Kg/Hr) | | | | | | | | | |
| $H_2$ | 1616 | 46 | 1616 | 1606 | 10 | 46 | 10 | | 10 |
| Methane | 700 | 110 | 649 | 615 | 34 | 59 | 85 | | 85 |
| Ethylene | 109 | 39 | 80 | 67 | 13 | 10 | 42 | | 42 |
| Ethane | 133 | 56 | 88 | 67 | 21 | 11 | 66 | | 66 |
| Propylene | 2291 | 1496 | 915 | 377 | 538 | 120 | 1914 | 105 | 1809 |
| Propane | 2114 | 1445 | 769 | 251 | 518 | 100 | 1863 | 251 | 1612 |
| Isobutane | 28769 | 23749 | 5685 | 59 | 5626 | 665 | 28710 | 28676 | 34 |
| Isobutylene | 39011 | 32867 | 6940 | 50 | 6890 | 796 | 38961 | 38926 | 35 |
| n-Butylene | 1030 | 874 | 176 | | 176 | 20 | 1030 | 1030 | |
| Butadiene | 660 | 562 | 111 | | 111 | 13 | 660 | 660 | |
| n-Butane | 1720 | 1484 | 266 | | 266 | 30 | 1720 | 1720 | |
| $C_{5+}$ | 385 | 383 | 2 | | 2 | | 385 | 385 | |
| $CO_2$ | 588 | 198 | 444 | 372 | 72 | 54 | 216 | — | 216 |
| CO | 223 | 14 | 221 | 217 | 4 | 12 | 6 | — | 6 |
| $N_2$ | 3793 | 186 | 3775 | 3727 | 48 | 168 | 66 | — | 66 |
| Rate (Kg/Hr) | 83142 | 63509 | 21737 | 7408 | 14329 | 2104 | 75734 | 71753 | 3981 |
| Temperature (°C.) | | 40 | 40 | | 15 | 33 | 33 | | |
| Pressure (Kg/cm²Abs.) | | 31.3 | 31.3 | | 29.5 | 10.5 | 10.5 | | |

TABLE 2

RECOVERY OF BUTADIENE

| STREAMS | 10 | 28 | 29 | 31 | 39 | 42 | 43 | 51 | 53 |
|---|---|---|---|---|---|---|---|---|---|
| Composition (as flow rate Kg/Hr) | | | | | | | | | |
| $H_2$ | 2082 | 45 | 2093 | 2082 | 11 | 54 | 2 | — | 2 |
| Methane | 1350 | 184 | 1411 | 1350 | 61 | 199 | 46 | — | 46 |
| Ethylene | 1284 | 596 | 1508 | 1284 | 224 | 465 | 355 | — | 355 |
| Ethane | 1283 | 883 | 1623 | 1283 | 340 | 588 | 635 | — | 635 |
| Propylene | 2631 | 8644 | 5452 | 2576 | 2876 | 2725 | 8795 | 55 | 8740 |
| Propane | 356 | 1518 | 723 | 261 | 462 | 402 | 1578 | 95 | 1483 |
| Isobutane | 1674 | 1696 | 327 | 17 | 310 | 191 | 1815 | 1657 | 158 |
| Isobutylene | 840 | 37 | 133 | 4 | 129 | 81 | 885 | 836 | 49 |
| Butene-1 | 13909 | 13781 | 2042 | 56 | 1986 | 1253 | 14514 | 13853 | 661 |
| Butadiene | 15949 | 15799 | 2249 | 48 | 2201 | 1399 | 16601 | 15901 | 700 |
| n-Butane | 56940 | 55682 | 6734 | 56 | 6678 | 4371 | 57989 | 56434 | 1555 |
| Butene-2 (trans) | 16438 | 16167 | 1700 | 17 | 1683 | 1111 | 16739 | 16421 | 318 |
| Butene-2 (cis) | 11801 | 11637 | 1332 | — | 1332 | 873 | 12096 | 11801 | 295 |
| $C_{5+}$ | 2709 | 2710 | 9 | — | 9 | 10 | 2709 | 2709 | — |
| $CO_2$ | 1607 | 667 | 1843 | 1607 | 236 | 527 | 376 | — | 376 |
| CO | 370 | 19 | 378 | 370 | 8 | 25 | 2 | — | 2 |
| $N_2$ | 5781 | 220 | 5893 | 5781 | 112 | 314 | 18 | — | 18 |
| Rate (Kg/Hr) | 136554 | 131085 | 35450 | 16792 | 18658 | 14588 | 135155 | 119762 | 15393 |
| Temperature (°C.) | | 40 | 40 | | 15 | 21 | 21 | | |
| Pressure (Kg/cm²Abs.) | | 31.2 | 31.2 | | 29.5 | 4.2 | 4.2 | | | drocarbons and lower-boiling components, said method comprising:
  (a) compressing and cooling the feed stream to 100-500 psig and 50°-150° F. in a compression train comprising one or more compressor stages, each stage consisting of a compressor, an aftercooler, and a vapor-liquid separator, thus producing a first compressed vapor stream and a first condensate stream;
  (b) cooling and partially condensing said first compressed vapor stream to yield a second vapor stream and a second condensate stream, said second condensate stream comprising from 1 to 30% of components having lower boiling points than said olefinic hydrocarbons;
  (c) combining said first and said second condensate streams and flash evaporating the combined stream at a pressure of 0 to 200 psig thus producing a third vapor stream and a liquid stream, wherein said third vapor stream comprises at least some of said lower-boiling components in said combined stream; and
  (d) separating said liquid stream by distillation to yield a vapor product containing substantially all of the lower-boiling components in said liquid stream and a liquid product rich in the olefinic hydrocarbons in said feed stream.

2. The method as recited in claim 1 wherein said flash evaporation step (c) is conducted adiabatically.

3. The method as recited in claim 1 wherein said flash evaporation step (c) is conducted at a pressure of 50 to 150 psig.

4. The method as recited in claim 1 wherein said condensation step (b) includes cooling said first compressed vapor stream sufficiently to produce a condensate comprising from 5 to 15% of said lower-boiling components.

5. The method as recited in claim 1 wherein said feed stream comprises isobutylene and wherein said distillation step (d) is carried out at a pressure between 0 and 200 psig, whereby substantially all isobutylene in said feed stream is recovered in said liquid product.

6. The method is recited in claim 1 wherein said feed stream comprises butadiene and wherein said distillation step (d) is carried out at a pressure such that the reboiler temperature of said distillation step does not exceed 150° F., whereby substantially all butadiene in said feed stream is recovered in said liquid product.

7. The method as recited in claim 1 wherein said feed stream comprises propylene and wherein said distillation step (d) is carried out at a pressure between 300 and 400 psig, whereby substantially all propylene in said feed stream is recovered in said liquid product.

8. The method as recited in claim 1 wherein said feed stream comprises isopentadiene (isoprene) and wherein said distillation step (d) is carried out at a pressure between 50 and 150 psig, whereby substantially all isopentadiene (isoprene) in said feed stream is recovered in said liquid product.

9. The method as recited in claim 1 wherein said distillation step (d) is conducted at a pressure at or higher than said pressure of said flash evaporation step (c).

10. The method as recited in claim 1 wherein some or all of said third vapor stream from said flash evaporation step (c) is recycled to said compression step (a).

11. The method as recited in claim 1 wherein some or all of said vapor product from said distillation step (d) is recycled to said compression step (a).

12. The method as recited in claim 1 wherein some or all of said third vapor stream from said flash evaporation step (c) is recycled to said compression step (a) and some or all of said vapor product from said distillation step (d) is recycled to said compression step (a).

13. The method as recited in claim 1 wherein at least a portion of the cooling for said cooling step (b) is provided by adiabatic expansion of at least a portion of said first compressed vapor stream from compression step (a).

14. The method as recited in claim 1 wherein at least a portion of the cooling for said cooling step (b) is provided by further compressing a portion of said first compressed vapor stream, expanding it adiabatically, and mixing it with the remaining portion of said first compressed vapor stream.

15. The method as recited in claim 1 wherein at least a portion of the cooling for said cooling step (b) is provided by heat exchange with an external refrigerant.

16. An apparatus for recovering one or more olefinic hydrocarbons each having three, four, or five carbon atoms from a feed stream comprising said olefinic hydrocarbons and lower-boiling components, said apparatus comprising:
  (a) piping means to supply said feed stream;
  (b) compression means comprising at least one compression stage, said compression stage consisting of a compressor, an aftercooler, and a vapor-liquid separator, by which a first compressed vapor stream and a first condensate stream are produced from said feed stream;
  (c) means for cooling and partially condensing said first compressed vapor stream to produce a second vapor stream and a second condensate stream, said cooling means being sufficient to produce said second condensate stream comprising from 1 to 30% of the lower-boiling components in the feed stream;
  (d) means for flash evaporating a combined liquid stream comprising said first and said second condensate streams to yield a third vapor stream and a liquid stream, whereby said third vapor stream comprises at least some of said lower-boiling components in said combined stream;
  (e) distillation means for separating said liquid stream to yield a vapor product comprising substantially all of the lower-boiling components present in said liquid stream and a liquid product rich in the olefinic hydrocarbons in said feed stream;
  (f) means for recycling some or all of said third vapor stream from said flash evaporation step to said compression means;
  (g) piping means for removing said vapor product from said distillation means; and
  (h) piping means for removing said liquid product from said distillation means.

17. The apparatus as recited in claim 16 further comprising means for recycling some or all of said vapor product from said distillation means to said compression means.

* * * * *